United States Patent [19]
Grollier et al.

[11] Patent Number: 6,136,332
[45] Date of Patent: *Oct. 24, 2000

[54] DERMATOLOGICAL/PHARMACEUTICAL COMPOSITIONS COMPRISING VOLATILE OILS/PHENYLATED SILICONE OILS

[75] Inventors: Jean-François Grollier, Paris; Josiane Allec, Antibes; Isabelle Agostini, Chatenay Malabry, all of France

[73] Assignee: Societe L'Oreal S.A., Paris, France

[ * ] Notice: This patent is subject to a terminal disclaimer.

[21] Appl. No.: 08/688,027

[22] Filed: Jul. 29, 1996

[30] Foreign Application Priority Data

Jul. 28, 1995 [FR] France ..................... 95 09252

[51] Int. Cl.$^7$ ............ A61K 9/10; A61K 47/30; A61K 47/44
[52] U.S. Cl. ............ 424/404; 424/486; 514/969; 514/937
[58] Field of Search .................... 424/486, 405, 424/409, 404; 514/937, 772.5, 969

[56] References Cited

U.S. PATENT DOCUMENTS

| | | |
|---|---|---|
| 5,413,792 | 5/1995 | Ninomiya et al. . |
| 5,444,096 | 8/1995 | McCrea et al. . |
| 5,523,091 | 6/1996 | Pastour et al. . |
| 5,531,986 | 7/1996 | Shevade et al. . |
| 5,556,613 | 9/1996 | Arnaud et al. . |
| 5,599,800 | 2/1997 | Candau et al. . |
| 5,637,306 | 6/1997 | Cauwet et al. . |

FOREIGN PATENT DOCUMENTS

| | | |
|---|---|---|
| 0150914 | 8/1985 | European Pat. Off. . |
| 0197485 | 10/1986 | European Pat. Off. . |
| 0336902 | 10/1989 | European Pat. Off. . |
| 0602905 | 6/1994 | European Pat. Off. . |

OTHER PUBLICATIONS

Chemical Abstracts, vol. 119, No. 22, Nov. 29, 1993; Abstract No. 233712Z, P. 537.

Patent Abstracts of Japan, vol. 10, No. 230 9C–365) [2286], Aug. 9, 1986.

*Primary Examiner*—Edward J. Webman
*Attorney, Agent, or Firm*—Burns, Doane, Swecker & Mathis, L.L.P.

[57] ABSTRACT

Transfer/migration-resistant, topically applicable dermatological/pharmaceutical compositions well suited for preventatively and/or curatively therapeutically treating human skin or mucous membranes, comprise at least one volatile oil, at least one phenylated silicone oil and at least one dermatologically and/or pharmaceutically bioaffecting active agent, for example at least one anviral, antibacterial, antifungal, anti-inflammatory, neuromediator modulator, etc.

33 Claims, No Drawings

DERMATOLOGICAL/PHARMACEUTICAL COMPOSITIONS COMPRISING VOLATILE OILS/PHENYLATED SILICONE OILS

CROSS-REFERENCE TO COMPANION APPLICATIONS

Copending applications Ser. No. 08/687,996 and Ser. No. 08/690,643, each filed concurrently herewith, and each assigned to the assignee hereof.

BACKGROUND OF THE INVENTION

1. Technical Field of the Invention

The present invention relates to novel dermatological/pharmaceutical compositions for topical application, for preventively and/or curatively treating afflicted human skin or mucous membranes, in particular for treating afflicted lips.

2. Description of the Prior Art

It is known to this art that cutaneous or mucosal lesions, especially of the lips, can be caused by an infection due to microorganisms, and in particular of viral, bacterial or fungal origin, by immunodependent or non-immunodependent inflammatory phenomena, by phenomena of neurogenic type, by cellular disfunctionings, such as disorders of proliferation, of differentiation or of pigmentation, and/or by external factors, such as cold, UV radiation, burns, the oral absorption of certain medicaments, allergens or irritants, or insect stings.

Various dermatological or pharmaceutical compositions for preventing such lesions and/or for therapeutically treating the affected region, as well as adjacent regions, after the appearance of such lesions, are also known. These compositions can, in particular, be provided in the form of pasty products, such as ointments, creams or gels, in the form of sticks or, alternatively, in the form of solutions to be applied locally.

However, it has been observed that, when topically applied onto the skin, these compositions suffer from the disadvantage of transferring. By "transferring" is meant that they are removed from the skin and/or lips, at least in part, and "transfer" to substrates with which they are contacted, thereby discoloring same, and, in particular, are transferred to glass, clothing or the skin.

One result of transfer is a mediocre persistence and a limited contact time of the dermatological or pharmaceutical composition on the skin region to be treated.

A second result is a not very attractive deposit on the substrate, in particular when it concerns a third party, with a possible staining of the substrate.

Another result is a risk of contamination, for the substrate, by the active agents and/or by the infectious agents present on the skin of the person treated.

It is thus necessary to regularly reapply the composition on the skin or the mucous membranes, while preventing contact with any substrate, to decrease the risk of transfer.

Another disadvantage presented by the compositions of the prior art is their tendency to migrate, namely, they have a tendency to spread towards regions adjacent to the treated region, in particular into the wrinkles of the skin, diffusing the active and/or infectious agents.

SUMMARY OF THE INVENTION

Accordingly, a major object of the present invention is the provision of improved dermatological/pharmaceutical compositions which avoid or conspicuously ameliorate the above disadvantages and drawbacks to date characterizing the state of this art, and which are deposited into films exhibiting very good hold, which transfer to only a minor extent or not at all and which migrate to only a minor extent, or indeed not at all.

Briefly, the present invention features topically applicable dermatological/pharmaceutical compositions comprising at least one volatile oil, at least one phenylated silicone oil and at least one dermatologically and/or pharmaceutically active agent.

This invention also features a process for the preparation of said compositions, comprising first preparing a premix containing at least a fraction of the various constituents of the composition, including any waxes. Such premix is heated, while mixing it, to a temperature at which it melts. The remainder of the constituents are next added at a suitable temperature, which can be on the order of room or ambient temperature, while continuing the mixing. The mixture obtained is then mixed over at least a part of the time of its cooling to room temperature, if it was at a higher temperature, and wherein the mixing operation is carried out at least partially in at least one extruder.

The present invention also features the formulation of a combination of a volatile oil and of a phenylated silicone oil into a topically applicable dermatological or pharmaceutical composition comprising at least one dermatologically and/or pharmaceutically active agent, for the purpose of improving the transfer and/or migration resistance of said composition.

DETAILED DESCRIPTION OF BEST MODE AND SPECIFIC/PREFERRED EMBODIMENTS OF THE INVENTION

More particularly according to the present invention, it has been observed that the subject compositions are converted into homogeneous films which are readily applicable and which spread readily and uniformly. The resulting film exhibits a light texture and is comfortable to wear throughout the day.

Prolonged contact time of the active agent with the region treated is thus promoted, as is the penetration of certain medicaments.

Moreover, the presence of the compositions of the invention on the treated areas of the skin and/or lips permits maintaining reduced humidification, and is favorable to accelerated treatment of the affliction. The compositions according to the invention can, in addition, advantageously be used to formulate active agents which are unstable in an aqueous medium.

The compositions of the invention thus comprise a volatile oil, selected in particular from among the cyclic or linear silicone oils or hydrocarbon oils, whether singly or in combination.

By "volatile oil" is intended any oil capable of evaporating on contact with the skin. Oils are preferably employed, the ignition points of which are sufficiently high to permit the formulation thereof and sufficiently low as to attain the desired evanescent effect. Oils in which the ignition point is on the order of 40°–100° C. are the preferred. Exemplary volatile silicone oils include cyclotetradimethylsiloxane, cyclopentadimethylsilioxane, cyclohexadimethylsiloxane and methylhexyldimethylsiloxane. And exemplary volatile hydrocarbon oils include the isoparaffins.

The compositions of this invention advantageously comprise from 8% to 80% by weight, preferably from 30% to 60% by weight, of volatile oils with respect to the total weight of the composition.

The compositions according to the invention also comprise a phenylated silicone oil. This oil can be a polyphenylmethylsiloxane or a phenyltrimethicone, or a mixture of various phenylated silicone oils and, in particular, can correspond to the following structural formula (I):

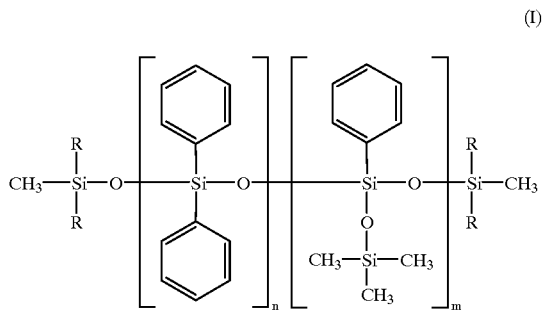

in which R is a $C_1$–$C_{30}$ alkyl radical, an aryl radical or an aralkyl radical; n is an integer ranging from 0 to 100; and m is an integer ranging from 0 to 100, with the proviso that the sum m+n ranges from 1 to 100.

R is preferably a methyl, ethyl, propyl, isopropyl, decyl, dodecyl or octadecyl radical, or, alternatively, a phenyl, tolyl, benzyl or phenethyl radical.

Exemplary such phenylated oils are the oil Belsil PDM1000 marketed by Wacker, the oils DC556 and SF558 marketed by Dow Corning, the oil Abil AV8853 marketed by Goldschmidt, or the oil Silbione 70633V30 marketed by Rhône-Poulenc.

The compositions of the invention advantageously comprise 1% to 35% by weight, preferably 20% to 30% by weight, of phenylated silicone oils.

The fatty phase can comprise, in addition to the above oils, the fatty substances conventional to this art. Exemplary thereof are silicone fatty substances, such as silicone oils, gums and waxes, and nonsilicone fatty substances, such as vegetable, mineral, animal and/or synthetic oils or waxes, and mixtures thereof. Preferred are occlusive or film-forming fatty substances which can promote the penetration of the active agent and the "screen" effect of the composition.

Exemplary silicone fatty substances include polydimethylsiloxanes (PDMS) and alkyldimethicones, as well as silicones modified by aliphatic and/or aromatic substituents, which are optionally fluorinated, or by functional groups such as hydroxyl, thiol and/or amine groups.

Exemplary of the nonsilicone fatty substances are liquid paraffin, liquid petrolatum, perhydrosqualene, arara oil, sweet almond oil, calophyllum oil, palm oil, castor oil, avocado oil, jojoba oil, olive oil or cereal germ oil; esters of fatty acids; alcohols; acetylglycerides; octanoates, decanoates or ricinoleates of alcohols or of polyalcohols; triglycerides of fatty acids; glycerides; hydrogenated oils which are solid at 25° C.; lanolins; fatty esters which are solid at 25° C.; beeswax; vegetable waxes, such as carnauba wax, candelilla wax, ouricury wax, japan wax or sugar cane or cork fiber waxes; mineral waxes, for example paraffin wax, lignite wax or microcrystalline waxes or ozokerites; or synthetic waxes, including polyethylene waxes and waxes obtained via the Fischer-Tropsch synthesis.

These fatty substances are variously selected by one skilled in this art to formulate a composition having the desired properties, for example with respect to consistency or texture.

In particular, the compositions according to the invention can comprise at least one wax, such as to impart mechanical strength when the composition is provided in the form of a stick. When it is provided in the form of a supple paste, or of a cast product produced by a conventional process, the compositions of the invention comprise a small amount of wax, for example on the order of 5%–12% by weight. When it is produced by extrusion, the composition can comprise a larger amount of waxes and, in particular, preferably 12%–60% by weight of waxes having a melting point greater than 55° C.

Generally, the subject compositions comprise 0.5%–30% by weight of at least one hydrocarbon and/or silicone wax and preferably 10%–20% by weight of hydrocarbon wax and 0%–10% by weight of silicone wax.

The compositions according to the present invention also comprise at least one biologically active agent or drug species. Exemplary thereof are pharmaceutical agents which are active against microorganisms, in particular having antiviral, antibacterial or antifungal activity; agents having anti-inflammatory or immunomodulating activity; agents which are antagonists of neuromediators, or which modulate the release of neuromediators; agents which modulate cell differentiation and/or cell proliferation and/or pigmentation and/or which regulate keratinization; agents which are active in the treatment and/or the prevention of cheilites; antihistamines; or healing agents.

Representative therapeutic agents having a degree of antiviral activity are the virostatic and/or virucidal agents, in particular agents which are active with respect to the class of Papillomaviruses, such as the HPV1 virus and/or the HPV2 virus. Also representative are the agents which are active with respect to the type 1 and/or type 2 herpes simplex virus.

More specifically representative of such bioaffecting agents are:

(1) purine derivatives, in particular guanine or adenine derivatives, and for example those which are substituted in the 9-position, such as:
  (i) 9-(2-hydroxyethoxymethyl)guanine (or Acyclovir), its salts or its esters, in particular acyclovir valerate or the esters of amino acids, such as valine or isoleucine, or of derivatives of amino acids, such as the N-substituted aminomethylbenzoic esters, such as the 4-morpholinobenzoic ester or 3-(or 4-) aminomethylbenzoic ester,
  (ii) 9-[4-hydroxy-3-(hydroxymethyl)butyl]guanine (or Penciclovir), its salts or its esters or diesters,
  (iii) 9-β-D-arabinofuranosyladenine (or Vidarabine), its salts or its esters, such as the 2'-acetic ester,
  (iv) 2-[2-(2-amino-9H-purin-9-yl)ethyl]-1,3-propanediol diacetate (or Famcyclovir) or its salts;
(2) pyrimidine derivatives, in particular uracil or cytosine derivatives, for example those which are substituted in the 1-position by a 2'-deoxyribofuranosyl substituent, such as:
  (i) alkyl-2'-deoxyuridines and in particular vinyl-2'-deoxyuridine, 5-ethyl-2'-deoxyuridine and 5-isopropyl-2'-deoxyuridine,
  (ii) 5-halo-2'-deoxyuridines and in particular 5-iodo-2'-deoxyuridine (or Idoxuridine) or its esters, such as the 5'-ethanoic or 5'-benzoic ester; 5-trifluoromethyl-2'-deoxyuridine (or Trifluridine); or 5-bromovinyl-2'-deoxyuridine;
  (iii) 5-iodo-2'-deoxycytidine (or Ibacitabine);
(3) guanidine derivatives, such as 4-morpholinecarboxyimidoylguanidine (or Moroxydine) or its salts;
(4) pyrophosphate analogs and their salts, such as phosphonoformic acid (or Foscarnet);

(5) peptides or proteins or glycoproteins which modulate and/or stimulate the immune response and which affect viral proliferation, such as the synthetic pentapeptide referred to as thymopentin or interferon-α, interferon-β or interferon-γ;

(6) metal salts, in particular of copper, gold, silver and/or lithium, and in particular lithium lactate or lithium succinate; and (7) antisense oligonucleotides, in particular those of the class of phosphonates or phosphorothioates.

Representative therapeutic agents having a degree of antibacterial activity are the bacteriostatic and/or bactericidal agents useful for the topical treatment of primary microbial infections, such as acne or peribuccal impetigo in infants, or secondary microbial infections, such as the infections which occur during the vesicular phase of herpes labialis.

More specifically representative of such bioaffecting agents are:

(1) agents of steroidal structure from the family of the fusidanines, such as fusidic acid and its salts;

(2) antibiotics, such as those:
  (i) from the family of the macrolides, such as erythromycin,
  (ii) from the family of the synergistins, such as virginiamycin,
  (iii) from the family of the lincosamides, such as clindamycin,
  (iv) from the family of the aminosides, such as neomycin, gentamycin or framycetin,
  (v) from the family of the rifamycins, such as rifamycin SV,
  (vi) of polypeptidic type from the family of the polymyxins, such as polymyxin B, and
  (vii) from the class of the tetracyclines, such as oxytetracycline or minocycline; and (3) antibacterials from the family of the quinolones, such as ciprofloxacin, enoxacin, ofloxacin, pefloxacin, rosoxacin, oxolinic acid, nalidixic acid, nadifloxacin or flumequine.

Representative therapeutic agents having a degree of antifungal activity are octopirox and cyclopirox; amorolfine; imidazoles, such as econazole, miconazole, omoconazole, itraconazole, fluconazole or ketoconazole; amphotericin B; tolnaftate; griseofulvin; terbinafine; or naftifine.

The bioaffecting agents having antiviral, antibacterial or antifungal activity advantageously constitute from 0.01% to 20% by weight of the total weight of the composition.

The therapeutic agents displaying anti-inflammatory activity according to the invention can also exhibit immunomodulating activity. Exemplary thereof are active agents of steroidal structure, such as clobetasol propionate, betamethasone valerate, hydrocortisone or hydrocortisone aceponate, or active agents of nonsteroidal structure, such as piroxicam, ibuprofen, enoxolone or bufexamac, or alternatively α-bisabolol.

They are advantageously present in the proportion of 0.01%–20% by weight of the composition.

Representative therapeutic agents which are antagonists of neuromediators or which modulate the release of neuromediators are the antipruritics, such as crotamiton; inhibitors of the release of neuropeptides and in particular of substance P, such as inhibitors of NK1; capsaicin and its analogs; and lithium salts.

These are advantageously present in the proportion of 0.01%–20% by weight of the composition.

Representative therapeutic agents which modulate cell differentiation and/or cell proliferation and/or pigmentation are substances which act via nuclear receptors, such as steroidal receptors, thyroidal receptors, receptors for retinoids and receptors for vitamin D, in particular 6-[3-(1-adamantyl)-4-methoxyphenyl]-2-naphthoic acid, tretinoin, isotretinoin, cis-9-retinoic acid, calcitriol, secalciferol or calcipotriol, or substances which act on cell metabolism, such as anthralin.

Exemplary therapeutic agents which modulate cutaneous pigmentation are the depigmenting agents, such as hydroquinone, kojic acid or caffeic acid; repigmenting agents, such as DHA or melanin precursors; or photosensitizing agents, such as 8-methoxypsoralen.

These are advantageously present in the proportion of 0.001% to 10% by weight of the composition.

Exemplary therapeutic agents which regulate keratinization are the hydroxy acids, such as lactic acid, citric acid or glycolic acid, salicylic acid or derivatives thereof, or alternatively 2-hydroxy-5-octanoylbenzoic acid.

These are advantageously present in the proportion of 0.1% to 30% by weight of the composition.

Exemplary therapeutic agents which are active in the treatment and/or the prevention of cheilites, in particular when caused by the weather or when of mechanical or iatrogenic origin are derivatives of mandelic acid, such as α-acetylmandelic acid.

These are advantageously present in the proportion of 0.1%–10% by weight of the composition.

And exemplary healing agents are, for example, vitamins A, E or F or their esters, certain peptides, growth factors or allantoin.

These are advantageously present in the proportion of 0.1%–10% by weight of the composition. They make it possible to prevent, to limit, or to treat the splitting or the bleeding of the lips due to cold or associated with the scabs present on the lips in the final phase of herpes labialis.

Representative antihistamines include promethazine, mefenidramium, triprolidine, cinnarizine and diphenyhydramine.

These are advantageously present in the proportion of 0.01%–10% by weight of the composition.

Depending on the pathologies to be treated, it may be judicious to combine a number of active agents or, alternatively, to add supplementary active agents thereto which will promote the prevention or the treatment of the ailment and/or will treat symptoms associated with such ailment.

Representative supplementary active agents include local anaesthetics, antiseptics, moisturizers and/or emollients, and sunscreening agents, in particular organic or inorganic sunscreening agents.

Exemplary of the local anaesthetics are lidocaine or tetracaine.

These are advantageously present in the proportion of 0%–10% by weight of the composition and make it possible to decrease sensations of burning/pain, as well as the pruritus associated with certain infections.

Representative antiseptics include the bacteriostatic disinfectants from the class of the carbanilides, such as triclocarban; hexamidine diisethionate; quaternary ammonium derivatives, such as benzalkonium chloride; or chlorhexidine gluconate. Antiseptics constitute an adjunct treatment for originally bacterial afflictions or afflictions capable of developing a secondary infection; these are advantageously present in the proportion of 0%–20% by weight of the composition.

Exemplary moisturizing, lubricating or emollient agents include the polyols, lipoamino acids and certain fatty substances, such as sweet almond oil or karite butter.

These are advantageously present in the proportion of 0% to 20% by weight of the composition.

Exemplary organic sunscreening agents which absorb in the UVA and/or UVB include the cinnamic derivatives, such as octyl methoxycinnamate, or 2-ethylhexyl 2-cyano-3,3-diphenylacrylate, or 3,4-methylbenzylidene-2-bornanone, or 4-tert-butyl-4'-methoxydibenzoylmethane.

Inorganic sunscreening agents include certain inorganic pigments, such as metal oxides, in particular optionally coated titanium dioxide. The composition can comprise 0% to 15% by weight of sunscreening active agent.

Thus, in a preferred embodiment of the invention, the composition comprises the combination of an antiviral active agent with an organic and/or inorganic sunscreening agent and, in particular, a titanium dioxide.

The subject compositions can also contain an agent which promotes the solubilization or the compatibility of the active agents with the excipient of the composition (vehicle, carrier of diluent) and/or which promotes the penetration of said active agents into the skin or the mucous membranes. These include, for example, isopropyl myristate, oleic acid, lecithin or certain alcohols or glycols.

The subject compositions can also comprise a particulate phase which can contain pigments and/or fillers.

The pigments are advantageously present in the composition in the proportion of 0% to 10% by weight thereof. They can be white or colored, inorganic and/or organic. Representative inorganic pigments are titanium, zirconium or cerium dioxides, as well as zinc, iron or chromium oxides or ferric blue. These pigments can also be coated or can comprise the coating, in particular for mica particles; exemplary is mica coated with titanium dioxide, with iron oxide or with natural pigment, as well as colored titanium dioxide-coated mica.

Exemplary organic pigments include carbon black and barium, strontium, calcium and aluminum lakes.

The fillers, which are advantageously present in the proportion of 0% to 30% by weight, can be inorganic or synthetic, lamellar or non-lamellar. Exemplary thereof are talc, mica, silica, kaolin, nylon and polyethylene powders, Teflon, starch, titanium (di)oxide-coated mica, natural mother-of-pearl, boron nitride or microspheres, such as Expancel (Nobel Industrie), Polytrap (Dow Corning) and silicone resin microbeads (Tospearls marketed by Toshiba, for example).

The subject compositions can additionally comprise any additive or adjuvant conventionally employed in the art, such as antioxidants, fragrances, essential oils, preservatives, vitamins, dyes, essential fatty acids, sphingoceryls, surfactants or liposoluble polymers, such as polyalkylenes, polyacrylates and silicone polymers compatible with the fatty substances. These additives are advantageously present in the composition in the proportion of 0%–10% by weight.

One skilled in this art will of course take the care to select all possible additional compounds, namely, the supplementary active agents, the agents promoting solubilization, the compounds of the particulate phase and the additives and adjuvants, as well as the amounts thereof, such that, on the one hand, the advantageous properties of the composition according to the invention are not, or are only slightly, impaired by the intended addition and, on the other, that such additions remain compatible with the nature of the composition and the topical application thereof.

The compositions according to the invention can be provided in the form of a product or preparation for caring for or treating the skin and mucous membranes. They can, in particular, be provided in the form of a liquid or fluid, oily or gelled composition, of a supple paste or of a hard and cast paste, such as a stick.

By "supple paste" is intended a paste having a measurable viscosity, in contrast to the solid structure of a stick, where the viscosity cannot be measured. Such supple paste have a dynamic viscosity at 25° C. advantageously ranging from 3 to 35 Pa.s, measured using a Conraves TV rotary viscometer equipped with an "MS-r4" rotor, at the frequency of 60 Hz.

The compositions of this invention can be formulated according to processes which do not differ in any way from the processes which are conventionally used, in particular in the cosmetics arts or in topical pharmaceuticals, and which are well known to these arts. These processes comprise mixing the various constituents of the composition, heated beforehand generally to 95°–100° C. when waxes are present, and then, optionally, casting them according to the desired form before cooling.

Some constituents of the composition can be introduced at a lower temperature, in particular when they are heat-sensitive. However, it is not generally possible to incorporate same while cold without observing at least partial crystallization and/or solidification of the waxes present.

In this instance, and in particular when waxes are present in the composition, it is possible to prepare it by virtue of a process which employs at least one mixer/extruder.

According to this process, a premix comprising at least a fraction of the various constituents of the composition, including the waxes, if present, is first prepared. This premix can be heated, while mixing same, to a temperature at which it melts; the remainder of the constituents can then be added at a suitable temperature, which can be on the order of room temperature, in one or a number of steps, while continuing the mixing. The mixture obtained can then be mixed during at least a part of its cooling to room temperature, if it was at a higher temperature.

The mixing operation is carried out at least partially in an extruder.

The volatile oil is preferably added at the end of the extrusion process, at room temperature. However, the volatile oil can also be added during the cooling stage, preferably at a temperature of less than or equal to approximately 45° C.

This process makes it possible to obtain a composition which exists in the form of a supple paste, which is homogeneous and in which all the constituents are suitably mixed, without having to heat the heat-sensitive constituents to an excessively high temperature.

The heating operation can be carried out according to any known technique.

In a preferred embodiment of the invention, the heating and mixing, indeed cooling, operations are carried out completely in one or a plurality of extruders arranged in series, and preferably in a single twin-screw extruder.

Moreover, it too is possible, by adapting the outlet die of the mixer/extruder, to package the composition in line at the outlet of said mixer/extruder.

The conditions under which the extrusion can be carried out are described in FR-94/00756, hereby expressly incorporated by reference.

The present invention, thus, also features the dermatological or pharmaceutical treatment of the skin and/or of the mucous membranes comprising topically applying thereto a therapeutically effective amount of a composition as described above.

In order to further illustrate the present invention and the advantages thereof, the following specific examples are given, it being understood that same are intended only as illustrative and in nowise limitative.

EXAMPLE 1

A lipstick was prepared which had the following composition:

| | Fatty phase: | |
|---|---|---|
| (a) | Cyclopentadimethylsiloxane | 42 g |
| (b) | Polyphenylmethylsiloxane (DC556 Fluid marketed by Dow Corning) | 25 g |
| (c) | Silicone waxes | 10 g |
| (d) | Hydrocarbon waxes (in particular polyethylene) | 10 g |
| | Pulverulent phase: | |
| (e) | Titanium dioxide | 5 g |
| (f) | Fillers (Nylon powder, starch) | 2 g |
| | Active agents: | |
| (g) | Idoxuridine | 1 g |
| (h) | 3,4-Methylbenzylidenebornanone | 3 g |
| (i) | 4-tert-Butyl-4'-methoxydibenzoylmethane | 2 g |

The composition was formulated in the usual manner, by heating the fatty substances, except the volatile oils, to 95°–100° C. and mixing same.

The titanium dioxide and the fillers were then added.

The combined contents were next mixed using a Moritz turbine mixer at the rate of 3,000 rev/min. The volatile oils and the active agents, dispersed beforehand in an aliquot of oily phase, were added just prior to casting. The mixture was then cast in suitable molds.

A lipstick was thus obtained, having a pleasant texture, which spread well and was uniformly applied. The film was comfortable to wear on a long-term basis and did not migrate.

This stick is useful for the prevention of recurrent herpes labialis, in particular by daily application, for decreasing the frequency of the recurrences and the duration of the herpes eruptions.

EXAMPLE 2

A supple paste was formulated which had the following composition:

| (a) | Cyclopentadimethylsiloxane | 45 g |
|---|---|---|
| (b) | Polyphenylmethylsiloxane (DC556 Fluid marketed by Dow Corning) | 25 g |
| (c) | Silicone wax | 10 g |
| (d) | Polyethylene wax | 5 g |
| (e) | Alkyl dimethicone | 5 g |
| (f) | Titanium dioxide | 5 g |
| (g) | Fillers (in particular nylon powder) | 3 g |
| (h) | Anhydrous fusidic acid | 2 g |

The composition was formulated in the usual manner, by heating the fatty substances, except the volatile oils, to 95–100° C. and mixing same.

The titanium dioxide and the fillers were then added.

The combined contents were mixed using a Moritz turbine mixer at the rate of 3,000 rev/min.

The volatile oils and the fusidic acid, dispersed beforehand in an aliquot of oily phase, were added just prior to casting. The mixture was then cast in suitable packaging.

A supple paste was thus obtained, having a pleasant texture, which spread well and was uniformly applied. The film was comfortable to wear on a long-term basis and did not migrate.

This composition is useful for the treatment of bacterial infections which afflict the face, such as peribuccal impetigo in infants.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A substantially non-aqueous topically applicable dermatological/pharmaceutical composition that is substantially resistant to transfer or migration upon topical application to human skin or mucous membranes, which is adopted for preventatively and/or curatively therapeutically treating the skin or mucous membranes, wherein said resistance to transfer or migration is the result of the combination of at least one volatile oil, and at least one phenylated silicone oil contained in an amount effective to render said composition resistant to transfer or migration upon topical administration to human skin or mucous membranes, which composition further comprises a preventatively and/or curatively therapeutically effective amount of at least one dermatologically and/or pharmaceutically bioaffecting active agent, wherein the amount of said at least one phenylated silicone oil ranges from 20 to 35% by weight.

2. The dermatological/pharmaceutical composition as defined by claim 1, said at least one volatile oil comprising a cyclic or linear silicone oil, or a hydrocarbon oil, or admixture thereof.

3. The dermatological/pharmaceutical composition as defined by claim 2, said at least one volatile oil comprising cyclotetradimethylsiloxane, cyclohexadimethylsiloxane, methylhexyldimethylsiloxane, an isoparaffin, or admixture thereof.

4. The dermatological/pharmaceutical composition as defined by claim 1, comprising from 8% to 80% by weight of said at least one volatile oil.

5. The dermatological/pharmaceutical composition as defined by claim 1, said at least one phenylated silicone oil having the structural formula (I):

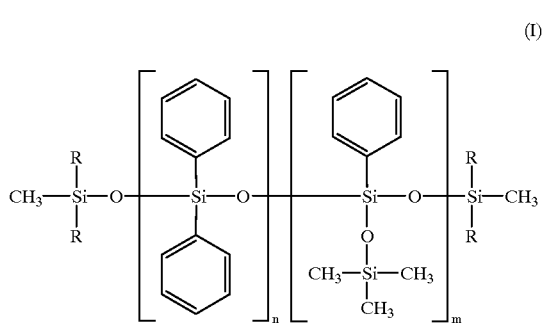

in which R is a $C_1$–$C_{30}$ alkyl radical, an aryl radical or an aralkyl radical; n is an integer ranging from 0 to 100; and m is an integer ranging from 0 to 100, with the proviso that the sum m+n ranges from 1 to 100.

6. The dermatological/pharmaceutical composition as defined by claim 1, comprising from 1% to 35% by weight of said at least one phenylated silicone oil.

7. The dermatological/pharmaceutical composition as defined by claim 1, said at least one bioaffecting active agent comprising an agent which is active against microorganisms, an agent having anti-inflammatory or immunomodulating activity, an agent which is an antagonist of neuromediators or which modulates the release of neuromediators, an agent which modulates cell differentiation and/or cell proliferation and/or pigmentation and/or which regulates keratinization, an agent which is active for the treatment and/or the prevention of cheilites, an antihistamine, a healing agent, or combination thereof.

8. The dermatological/pharmaceutical composition as defined by claim 7, said at least one bioaffecting active agent comprising an agent which is active against Papillomaviruses, an agent which is active against type 1 and/or 2 herpes simplex virus, an antiviral purine derivative, an antiviral pyrimidine derivative, an antiviral guanidine derivative, an antiviral pyrophosphate analog or salt thereof, an antiviral peptide or protein or glycoprotein which modulates and/or stimulates the immune response and which affects viral proliferation, an antiviral metal salt, an antisense oligonucleotide, or combination thereof.

9. The dermatological/pharmaceutical composition as defined by claim 7, said at least one bioaffecting active agent comprising a fusidanine antibacterial, a macrolide antibiotic, a synergistin antibiotic, a lincosamide antibiotic, an aminoside antibiotic, a rifamycin antibiotic, a polymyxin antibiotic, a tetracycline antibiotic, a quinolone antibacterial, or combination thereof.

10. The dermatological/pharmaceutical composition as defined by claim 7, said at least one bioaffecting active agent comprising octopirox, cyclopirox, amorolfine, an antifungal imidazole, amphotericin B, tolnaftate, griseofulvin, terbinafine, naftifine, or combination thereof.

11. The dermatological/pharmaceutical composition as defined by claim 7, said at least one bioaffecting active agent comprising a steroidal anti-inflammatory, a nonsteroidal anti-inflammatory, α-bisabolol, or combination thereof.

12. The dermatological/pharmaceutical composition as defined by claim 7, said at least one bioaffecting active agent comprising an antipruritic, an inhibitor of the release of neuropeptides, capsaicin or analog thereof, a lithium salt, or combination thereof.

13. The dermatological/pharmaceutical composition as defined by claim 7, comprising from 0.01% to 20% by weight of at least one agent active against microorganisms, anti-inflammatory, antagonist of neuromediators, modulator of the release of neuromediators, or combination thereof.

14. The dermatological/pharmaceutical composition as defined by claim 7, said at least one bioaffecting active agent comprising a modulator of cell differentiation and/or cell proliferation and/or pigmentation, a drug species which acts on cell metabolism, a depigmenting or repigmenting agent, a photosensitizing agent, or combination thereof.

15. The dermatological/pharmaceutical composition as defined by claim 14, comprising from 0.001% to 10% by weight of said bioaffecting modulator.

16. The dermatological/pharmaceutical composition as defined by claim 7, said at least one bioaffecting active agent comprising a hydroxy acid keratinization regulator.

17. The dermatological/pharmaceutical composition as defined by claim 16, comprising from 0.1% to 30% by weight of said hydroxy acid keratinization regulator.

18. The dermatological/pharmaceutical composition as defined by claim 7, said at least one bioaffecting active agent comprising vitamin A, E or F, or ester thereof, a growth factor, allantoin, or combination thereof.

19. The dermatological/pharmaceutical composition as defined by claim 7, said at least one bioaffecting active agent comprising promethazine, mefenidramium, triprolidine, cinnarizine, diphenylhydramine, or combination thereof.

20. The dermatological/pharmaceutical composition as defined by claim 7, comprising from 0.01% to 10% by weight of at least one healing agent or antihistamine agent, or combination thereof.

21. The dermatological/pharmaceutical composition as defined by claim 7, said at least one bioaffecting active agent comprising a mandelic acid derivative active in the treatment and/or the prevention of cheilites.

22. The dermatological/pharmaceutical composition as defined by claim 21, comprising from 0.1% to 10% by weight of said mandelic acid derivative.

23. The dermatological/pharmaceutical composition as defined by claim 1, further comprising a least one local anaesthetic, antiseptic, moisturizer and/or emollient, and/or organic or inorganic sunscreening agent, or combination thereof.

24. The dermatological/pharmaceutical composition as defined by claim 23, comprising at least one antiviral active agent and at least one organic and/or inorganic sunscreening agent.

25. The dermatological/pharmaceutical composition as defined by claim 1, further comprising at least one agent which promotes the solubilization or the compatibility of the at least one bioaffecting active agent within the composition and/or which promotes the penetration of said at least one bioaffecting active agent into the skin or the mucous membranes.

26. The dermatological/pharmaceutical composition as defined by claim 1, comprising a liquid or fluid, oil or gel, supple paste, hard and cast paste, or stick product.

27. The topically applicable dermatological/pharmaceutical composition of claim 1, which comprises a supple paste having a dynamic viscosity at 25° C. which ranges from 3 to 35 Pa.s measured using a Contraves TV rotary viscometer equipped with an "MS-r4" rotor, at a frequency of 60 Hz.

28. The composition of claim 27, which converts into a homogeneous film upon application.

29. A topically applicable dermatological/-pharmaceutical composition according to claim 1, which further comprises 5 to 12% by weight of a wax.

30. The composition according to claim 29, wherein said wax has a melting point greater than 55° C.

31. The dermatological/pharmaceutical composition according to claim 1, which further comprises 10 to 20% by weight of at least one hydrocarbon wax and 0 to 10% by weight of at least one silicone wax.

32. The dermatological/pharmaceutical composition as defined by claim 1, wherein the amount of said at least one phenylated silicone oil ranges from 20 to 30% by weight and the amount of said at least one volatile oil ranges from 30 to 60% by weight.

33. A substantially non-aqueous topically applicable dermatological/pharmaceutical composition that is substantially resistant to transfer or migration upon topical application to human skin or mucous membranes, which is adopted for preventatively and/or curatively therapeutically treating the skin or mucous membranes, wherein said resistance to transfer or migration is the result of the combination of at least one volatile oil, and at least one phenylated silicone oil contained in an amount effective to render said composition resistant to transfer or migration upon topical administration to human skin or mucous membranes, which composition further comprises a preventatively and/or curatively therapeutically effective amount of at least one dermatologically and/or pharmaceutically bioaffecting active agent, wherein said composition is in the form of a supple paste having a dynamic viscosity at 25° C. ranging from 3 to 35 Pa.S, measured using a Contraves TV rotary viscosimeter equipped with a "MS-r4" rotor at a frequency of 60 Hz, and wherein said composition comprises an amount of wax ranging from 5 to 12% by weight of said composition, and the amount of said at least one volatile oil ranges from 8 to 80% by weight, and the amount of said at least one phenylated silicone oil ranges from 1 to 35% by weight of said composition.

* * * * *